(12) United States Patent
Amark et al.

(10) Patent No.: US 7,442,185 B2
(45) Date of Patent: Oct. 28, 2008

(54) AUTO-INJECTOR

(75) Inventors: Mikael Amark, Brottby (SE); Thomas Bergens, Ingaro (SE)

(73) Assignee: SHL Group AB, Nacka Strand (SE)

( * ) Notice: Subject to any disclaimer, the term of this patent is extended or adjusted under 35 U.S.C. 154(b) by 626 days.

(21) Appl. No.: 10/450,391

(22) PCT Filed: Dec. 14, 2001

(86) PCT No.: PCT/SE01/02770

§ 371 (c)(1),
(2), (4) Date: Jun. 13, 2003

(87) PCT Pub. No.: WO02/47746

PCT Pub. Date: Jun. 20, 2002

(65) Prior Publication Data

US 2004/0039336 A1    Feb. 26, 2004

(30) Foreign Application Priority Data

Dec. 14, 2000  (SE) .................................... 0004628

(51) Int. Cl.
*A61M 5/20* (2006.01)
(52) U.S. Cl. ..................................... 604/137; 604/198
(58) Field of Classification Search ......... 604/134–137, 604/117, 131, 110, 197–199
See application file for complete search history.

(56) References Cited

U.S. PATENT DOCUMENTS 5,137,516 A * 8/1992 Rand et al. .................. 604/136
5,176,643 A    1/1993 Kramer et al.
5,478,316 A * 12/1995 Bitdinger et al. ............ 604/135
5,540,664 A *  7/1996 Wyrick ....................... 604/136
6,210,369 B1   4/2001 Wilmot et al.

FOREIGN PATENT DOCUMENTS

| EP | 0 824 923 A1 | 2/1998 |
|---|---|---|
| JP | 3222962 | 10/1991 |
| JP | 07-222799 | 8/1995 |
| JP | 10507935 T | 8/1998 |
| WO | 95/35126 A1 | 12/1995 |
| WO | WO 9939759 A1 * | 8/1999 |

OTHER PUBLICATIONS

Japanese Notice of Grounds of Rejection, mailed Apr. 3, 2007, in connection with Japanese Patent Application No. 549314/2002.

* cited by examiner

*Primary Examiner*—Nicholas D Lucchesi
*Assistant Examiner*—Theodore J Stigell
(74) *Attorney, Agent, or Firm*—Potomac Patent Group PLLC

(57) ABSTRACT

A device for auto-injection of a dose of medicament, comprises a housing arranged to contain a medicament container therein and a contact part intended to be applied against an injection site, a needle cover surrounding a needle arranged to the medicament container and extending at least the length of the needle, spring elements for, upon activation, pushing the needle past the end of the cover as well as operating the medicament container to supply the dose of medicament, first locking elements for locking the spring elements in a pressurized state, first activating elements for, upon manual operation, releasing the spring elements for injection. There is a second locking element capable of locking the first activating element and a second activating element, capable of releasing the second locking element when the contact part is exposed to pressure.

7 Claims, 10 Drawing Sheets

AUTO-INJECTOR

TECHNICAL FIELD

The present invention relates to an auto-injection device intended for injection of a dose of medicament, comprising a housing arranged to contain a syringe therein and comprising a contact part intended to be applied against an injection site, a needle cover surrounding the needle of the syringe, spring means capable of, upon activation, pushing the needle through the needle cover as well as injecting the dose of medicament, first locking means capable of locking said spring means in a pressurised state, and first activating means capable of, upon manual operation, releasing said spring means for injection.

BACKGROUND OF THE INVENTION

Automatically, or semi-automatically activated, injection devices have been on the market for many years. One of the first types was intended for war-times, which type was activated by merely pressing or slamming the injector against a body part thereby activating it. The main concern was to have the medicament injected as fast as possible, without much concern for the patient or for safety aspects such as unintentional firing.

Since auto-injectors began to be used by "normal" patients, such as for example asthmatics, and also since the AIDS risk has become an important issue, the handling and safety aspects have become much more important. Patent document U.S. Pat. No. 5,085,642 discloses an auto-injector comprising a preloaded compression spring acting on a plunger, which in turn acts on a syringe. Before use the needle is protected inside the injector from being contaminated. In order to activate the injector a cap has to be removed so that a firing button may be available. When the firing button is depressed, the plunger is released, whereby it pushes the needle out of the cover and the medicament is discharged with the help of the compression spring.

With the auto-injector according to U.S. Pat. No. 5,085,642, once the cap has been removed, there is a pronounced risk of unintentional misfiring if the patient depresses the firing button before the injector is placed against the intended injection location. This may be fatal if the patient for example suffers from an acute allergic attack and requires an injection immediately in order to seize the attack. Further, with this injector, the needle is completely exposed after the injection, whereby there is a pronounced risk of being pierced or scraped by the needle.

Patent document U.S. Pat. No. 5,681,291 discloses an auto-injector comprising a first and a second device for performing the injection. The first device retracts a needle cover surrounding the needle before use into the injector housing when a predetermined force is placed on the injector, thereby exposing the needle so that it can be pushed into the patient. When the needle cover has been retracted a certain distance, the second device is activated, which acts on the plunger of the syringe for injecting the medicament. The injector may also be provided with a spring for extracting the needle cover from the housing once the injector is withdrawn from the injection site, thereby covering the needle after use. The needle cover may also be locked in that extracted position.

One drawback with the injector according to U.S. Pat. No. 5,681,291 is that the injector has to be pressed actively by the patient with a rather high force in order to overcome the holding force of the needle cover and for entering the needle into the body of the patient. This force is even more pronounced when an extracting spring is used. This in connection with necessary step of pulling free a flexible arm on the outside of the injector in order to activate it makes the handling of the device very cumbersome and not user-friendly nor easy to use. The patient needs to be very active and to perform a certain number of actions, some with considerable force, in order to inject the medicament. In a crisis situation, such as described above, there may be a risk that the patient fails to handle the injector properly. The injector is also not suitable for children because of this.

Another aspect with the injector according to U.S. Pat. No. 5,681,291 is that the needle cannot be kept from becoming contaminated since the needle cover has an opening in the injection direction. The needle may of course have a removable cover or sheath, but removal of that would constitute yet a step in order to activate the injector.

BRIEF DESCRIPTION OF THE INVENTION

The aim of the present invention is to provide an auto-injection device without the above mentioned drawbacks which is user-friendly, easy to use, with a high degree of safety and greatly reduces the risk of unintentional misfiring.

This aim is accomplished according to the present invention with an injection device according to claim 1. Further particular features of the present invention are apparent from the dependent claims.

With an auto-injection device according to the present invention several advantages are obtained. The main activating means, which releases the spring means that performs the ejection of the needle and the injection of the medicament can not be operated unless the injector is actually pressed against the injection site. It is thus required to perform a "two-step" operation in order to inject the medicament. First the injector is pressed against the injection site, whereby the locking of the activator or firing button is released. After that the button may be pressed whereby the spring-loaded syringe is activated and the medicament is injected. This reduces the risk that the injector is misfired before it is placed on the appropriate and desired location because the activator cannot be depressed unless there is a pressure on the contact part of the injector.

The design is also so that if the injector is lifted again after pressing it against the injection site, if for example the patient wishes to use another site, the activator is again locked, i e the activator is always locked when the contact part of the injector is not under pressure. Further, the "two-step" operation can not be done in the opposite way, i e by first pressing the activator and then pressing the injector against the injection site, thereby further preventing accidental misfiring of the injector. Even so the injector according to the invention is simple to use and user-friendly. There is no need for removing safety caps or bending away safety pins in order to activate the injector, the patient just have to press the injector against the desired injection location.

In a preferred embodiment of the invention, the contact part is the needle cover, which completely covers the needle before use. Upon injection, the needle penetrates the needle cover. This enables the needle to be kept sterile before use. There is thus no need for removal of such covers before injection. When the injection cycle is almost completed, the spring-loaded needle cover is released from the housing so that it can be pushed out around the needle upon withdrawal of the injector from the injection site. The needle of the injector of the present invention is thus never exposed or visible to the patient, which enhances the safety of the device and also provides a comfort aspect to patients that do not like to see needles, such as children. When the cover is pushed out, it is locked in that position, thereby preventing the needle to becoming exposed by pushing the needle cover back into the injector.

These and other aspects of, and advantages with, the present invention will become apparent from the following detailed description of the invention and from the accompanying drawings.

BRIEF DESCRIPTION OF THE DRAWINGS

In the following detailed description, reference will be made to the accompanying drawing where.

DETAILED DESCRIPTION OF THE INVENTION

Figure 1:
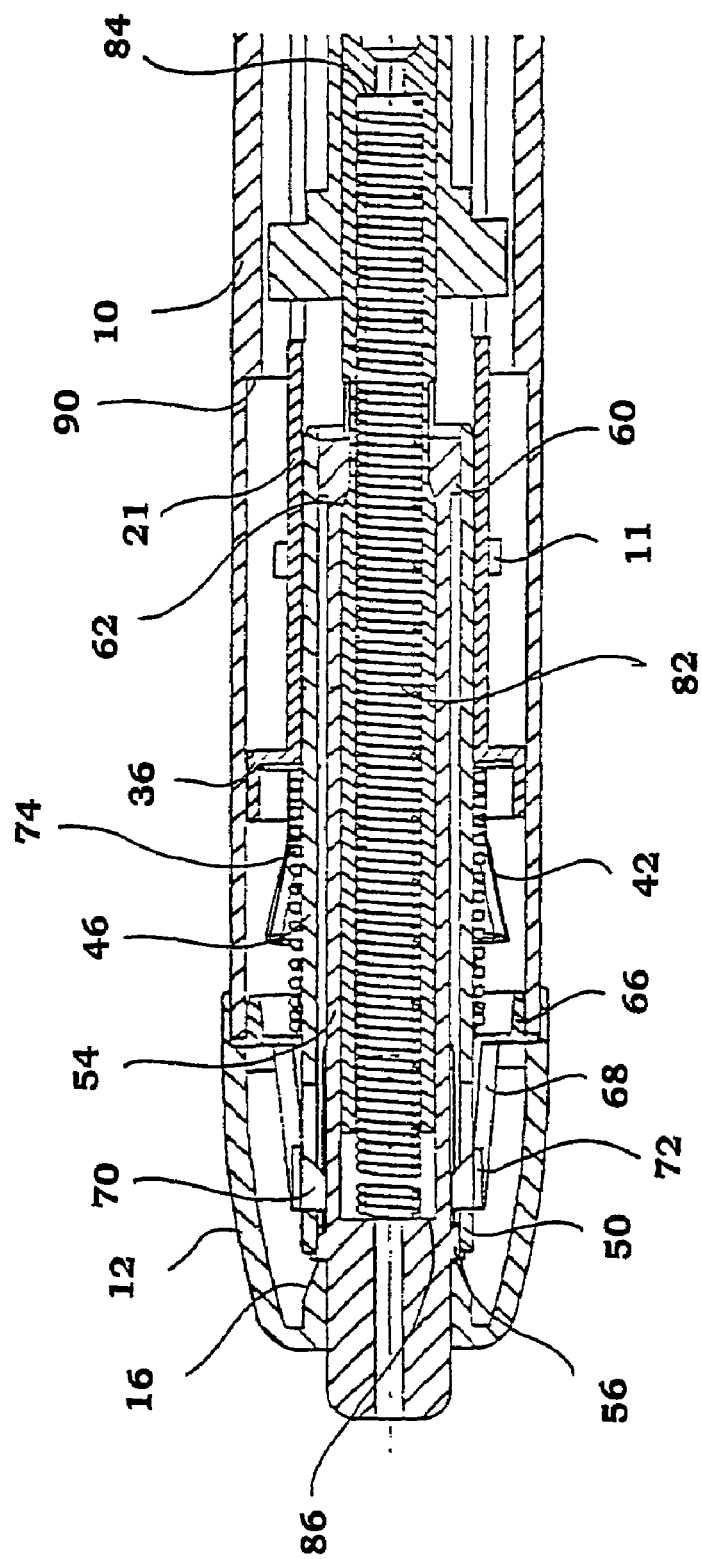
FIG. 1 is a cross-sectional view of the rear part of the auto-injector according to the invention.
Figure 2:
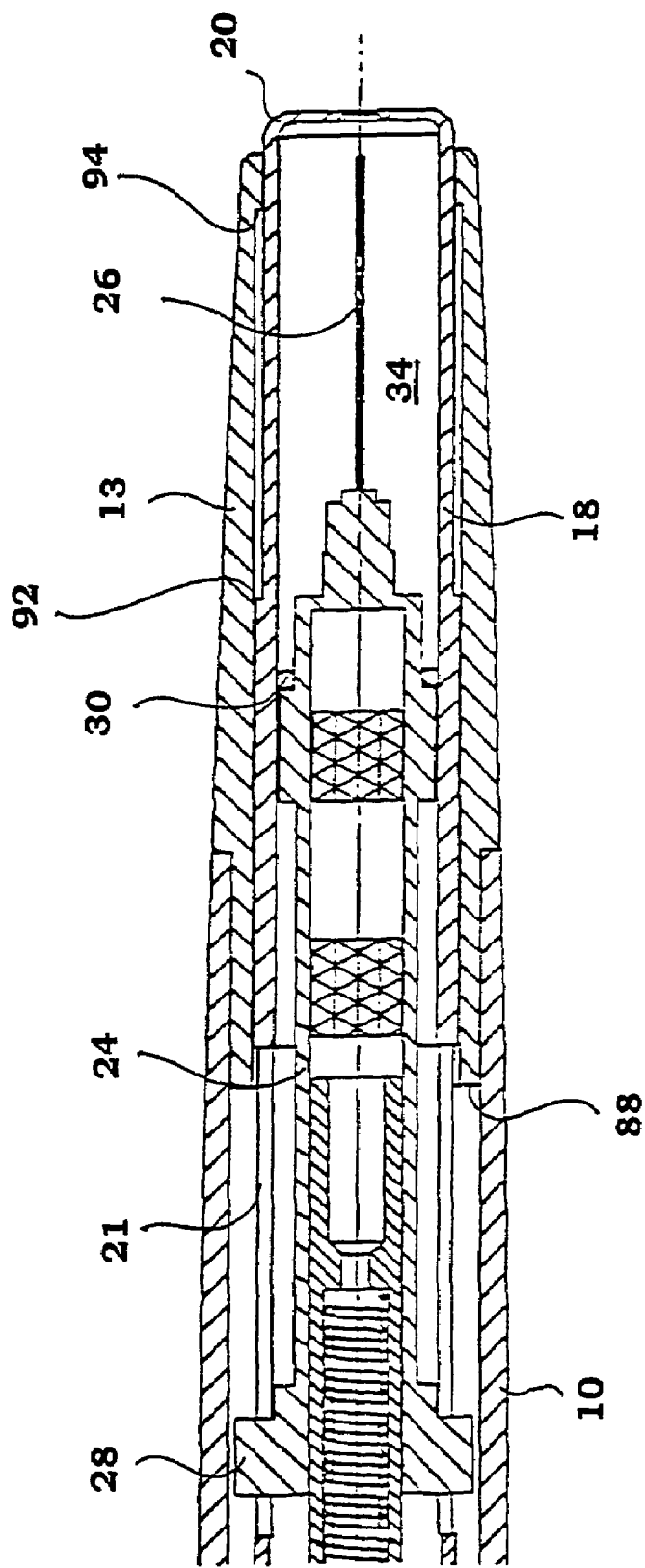
FIG. 2 is a cross-sectional view of the front part of the auto-injector according to FIG. 1.
Figure 3:
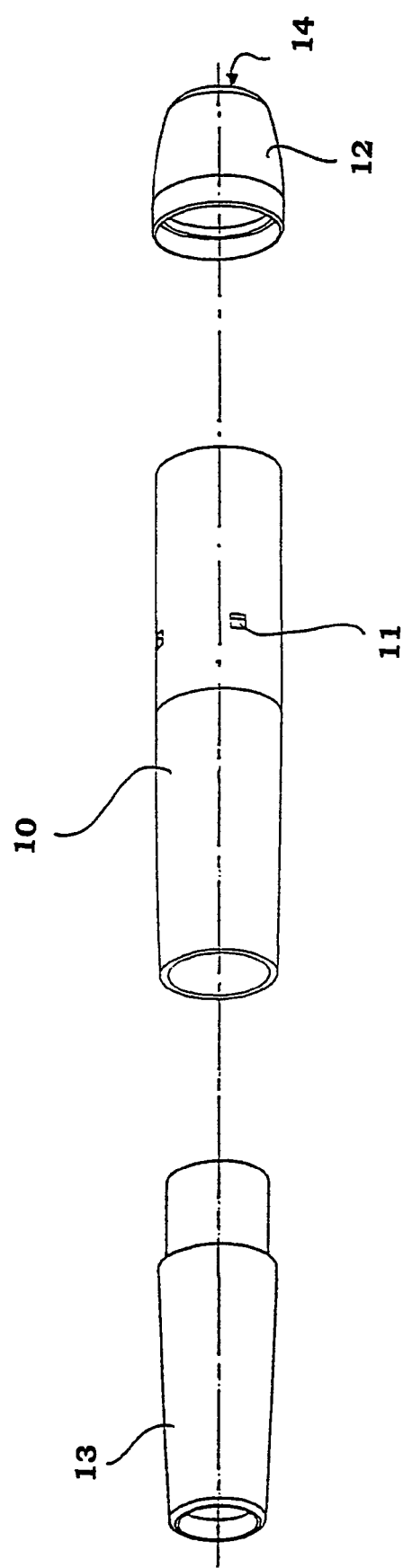
FIG. 3 is an exploded view of the housing part of the auto-injector according to FIG. 1.
Figure 4:
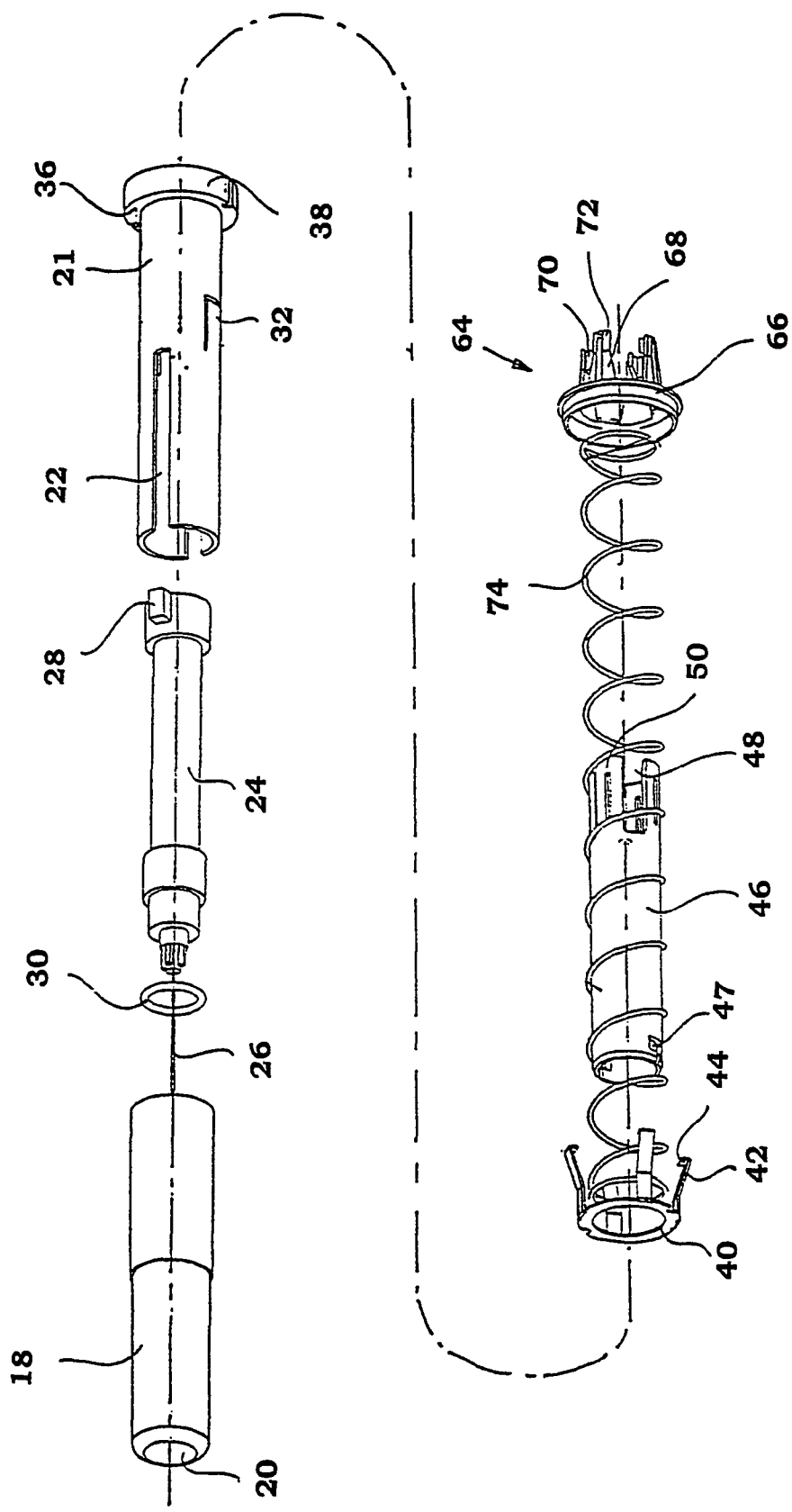
FIG. 4 is an exploded view of the injection mechanism of the auto-injector.
Figure 5:
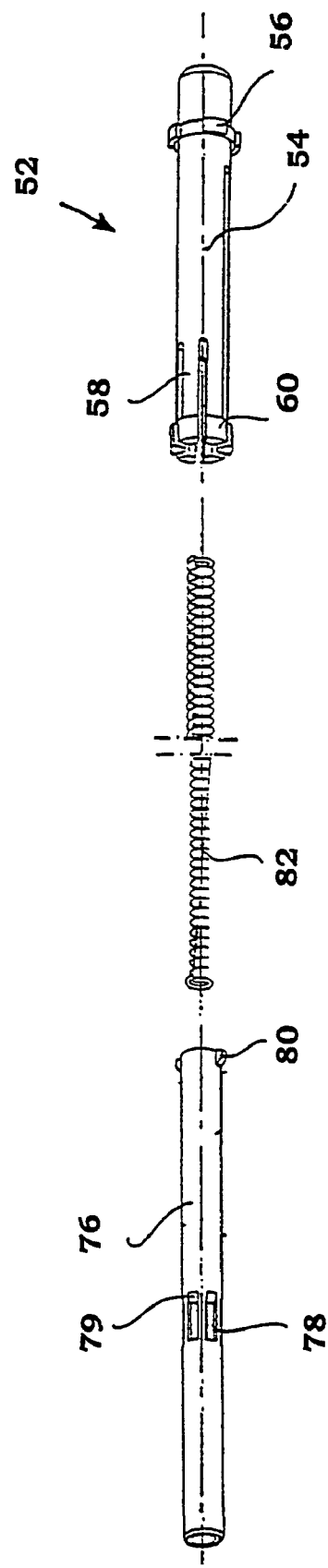
FIG. 5 is an exploded view of the force actuating means of the auto-injector.
Figure 6:
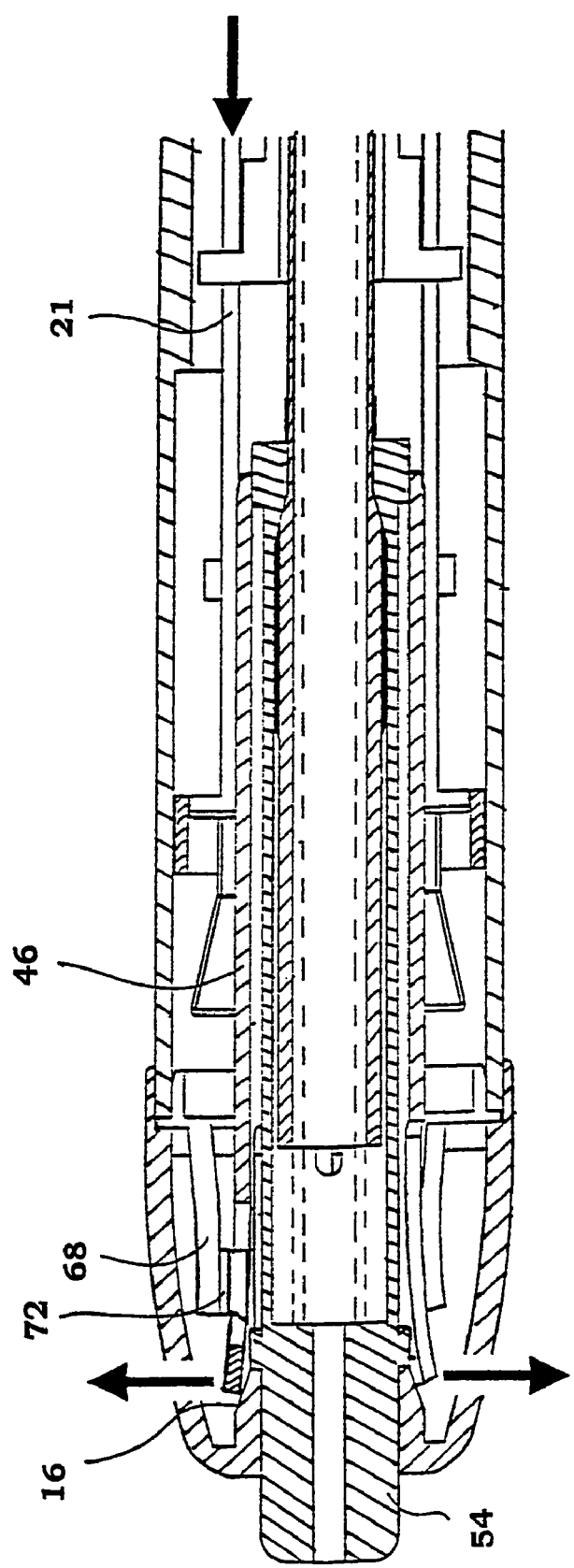
FIG. 6 shows the first step of activating the auto-injector of FIG. 1.

The injector according to a conceivable embodiment shown in the FIGS. 1-9 comprises an elongated generally tubular central housing 10 open at both ends. The central housing is provided with openings 11. One end of the housing is arranged with a front end piece 13 with a somewhat conical shape. The other end of the central housing is arranged with an end cap 12 attached to the housing. The end cap is provided with a tubular passage 14. The inner end of the tubular passage is arranged with conical surfaces 16. A tubular body 18, hereafter named needle cover, is slidably arranged in the front end piece and protruding a short distance from the end of the front end piece.

The end of the needle cover protruding from the front end piece is arranged with a closing end wall 20. Behind the needle cover, a tubular body 21, hereafter named front extension tube, is slidably arranged in the housing, where its front end is abutting the rear end of the needle cover. The front extension tube 21 is further provided with elongated slots 22 extending from the front end. A syringe 24 is arranged inside the needle cover with its needle 26 pointing at the end wall. That area of the end wall is preferably arranged thinner than the rest of the needle cover. The diameter of the syringe corresponds substantially to the inner diameter of the needle cover. The inner end of the syringe is provided with transversally arranged protrusions 28 adapted to fit into the elongated slots of the needle cover. A seal 30 is provided between the inside of the needle cover and the syringe and a circumferential ledge on the syringe body, thereby providing a closed sealed off space 34 for the needle.

The inner end of the front extension tube 21 is further provided with a circumferential outwardly directed ledge 36, which ledge is provided with a ring 38, where the inner diameter of the ring corresponds to the outer diameter of the ledge. A lock ring 40 is arranged abutting the ledge of the needle cover and provided with a number of legs 42 protruding backwards, to the left of FIG. 1, and somewhat outwards. The ends of the legs are provided with inwardly directed protrusions 44.

A tubular body 46, hereafter named rear extension tube, is arranged inside the rear part of the needle cover and extending some distance backwards, to the left of FIG. 1, from the needle cover. The rear extension tube is detachably connected to the front extension tube 21 via snap fits 32 on the front extension tube in recesses 47 on the surface of the rear extension tube. The rear part of the rear extension tube is arranged with a number of elongated slots 48, where some extend all the way to the end of the tube while some are left with some land 50. Inside the rear extension tube, an activator 52 is arranged. It comprises a generally tubular body 54 where one end protrudes through the passage of the end cap, forming an activation button. The activator is further provided with a number of protrusions 56 arranged around the circumference. The protrusions abut the end of the tubular passage with side surfaces. The opposite side surfaces of the protrusions are arranged somewhat conical inwardly. The other end of the activator is provided with a number of elongated slots, thereby forming a number of arms 58. The ends of he arms are arranged with outwardly directed projections 60, abutting the inner wall of the rear extension tube. The inner surface of the activator is generally cylindrical apart for a section near the inner end, to the right of FIG. 1, which is provided with a conically narrowing surface 62.

A locking mechanism 64 is further provided between the housing and the activator. It comprises a circular body 66 attached between the end cap and the housing. A number of arms 68 are arranged on the body, where the arms are protruding inwards and backwards as seen in FIG. 1. The ends of the arms are arranged with inwardly directed protrusions 70 which extend through those slots of the rear extension tube provided with land, whereby the backward facing surfaces of the protrusions abut against the conical surface of the ring of the activator. Preferably these surfaces are provided with the corresponding conicity. The arms are further provided with sidewardly extending protrusions 72, which rest against the outer surfaces of the rear extension tube adjacent the slots. A compression spring 74 is arranged between the locking mechanism 66 and the ledge of the front extension tube 21. Inside the activator, a plunger 76 is arranged, which plunger extends to, and abuts the plunger of the syringe. The plunger has a generally tubular shape and is arranged with a number of recesses 78, where each recess is provided with a conical surface 79, which conicity corresponds to the conical part 62 of the inner surface of the activator. The inner end of the plunger is arranged with two transversal protrusions 80 adapted to be arranged in the slots of the rear extension tube. A compression spring 82, shown with broken lines in the FIGS. 6-9, is arranged in the plunger between the activator and an inner stop surface 84 of the plunger.

The auto-injector is designed to function as follows. When the injector is loaded and ready to use, a syringe 24 is placed in the needle cover 18. Preferably the syringe with its needle and the inner surface 34 of the needle cover are sterilised after assembly. Due to the sealed-off space, because of the closed needle cover and the seal 30 between the syringe and the needle cover, the syringe is kept sterile.

The compression spring 82 is in a compressed state in the plunger 76 between its stop surface 84 and the end wall 86 of the activator. The plunger is prevented from moving due to that the arms 58 with projections 60 of the activator are abutting the inner surface of the rear extension tube 46 and that the conical surfaces of the plunger and the activator 62 and 78 are abutting each other.

In order to activate the injector, a two-step operation is needed, which enhances the security against misfiring. Firstly the injector has to be pressed with its injection end, the right end in FIG. 2, against the injection place, for example the leg of the patient. This causes the needle cover 18 and the front extension tube 21 to move inside the housing, FIG. 6, and thus the rear extension tube 46 since it is connected to the front extension tube. The end of the rear extension tube will come in contact with the conical surface 16 of the tubular passage, whereby the end of the rear extension tube will flex outwardly due to its slots 48. Because the arms 68 of the locking device rest on the outer surface of the rear extension tube, due to the sidewardly extending protrusions 72, the arms of the locking device also flex outwardly.

Figure 7:
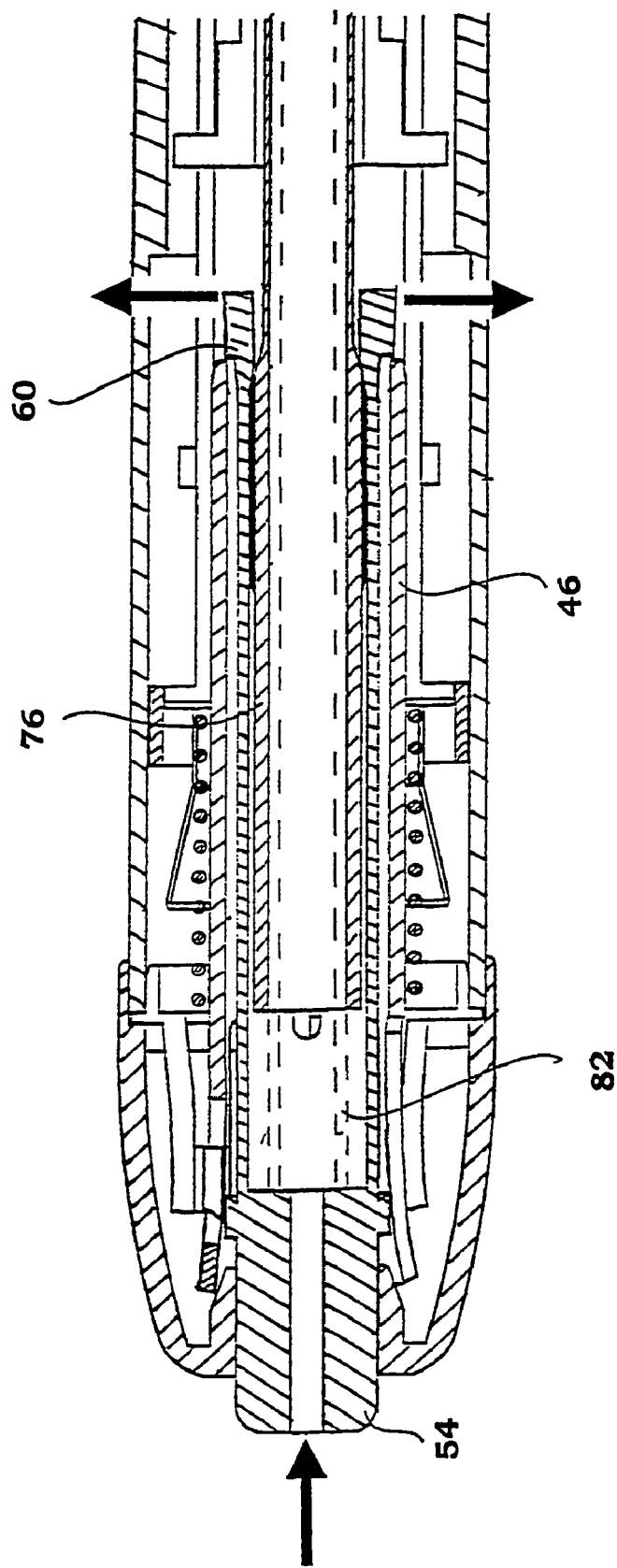
FIG. 7 shows the second step of activating the auto-injector.
Figure 8:
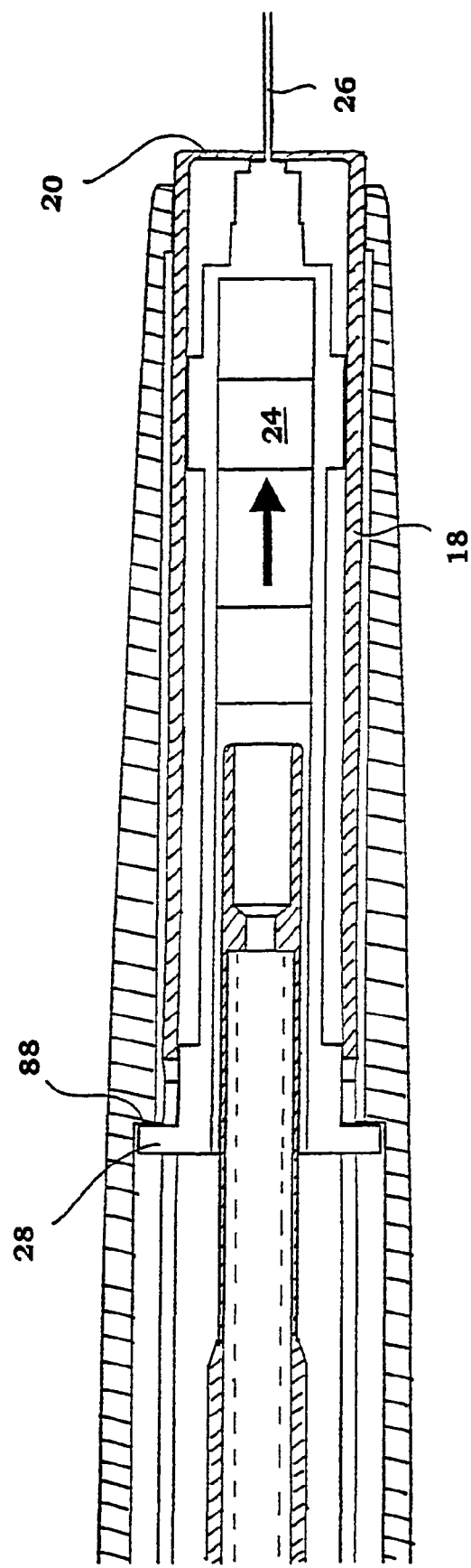
FIG. 8 shows the penetration of the needle of the auto-injector.
Figure 9:
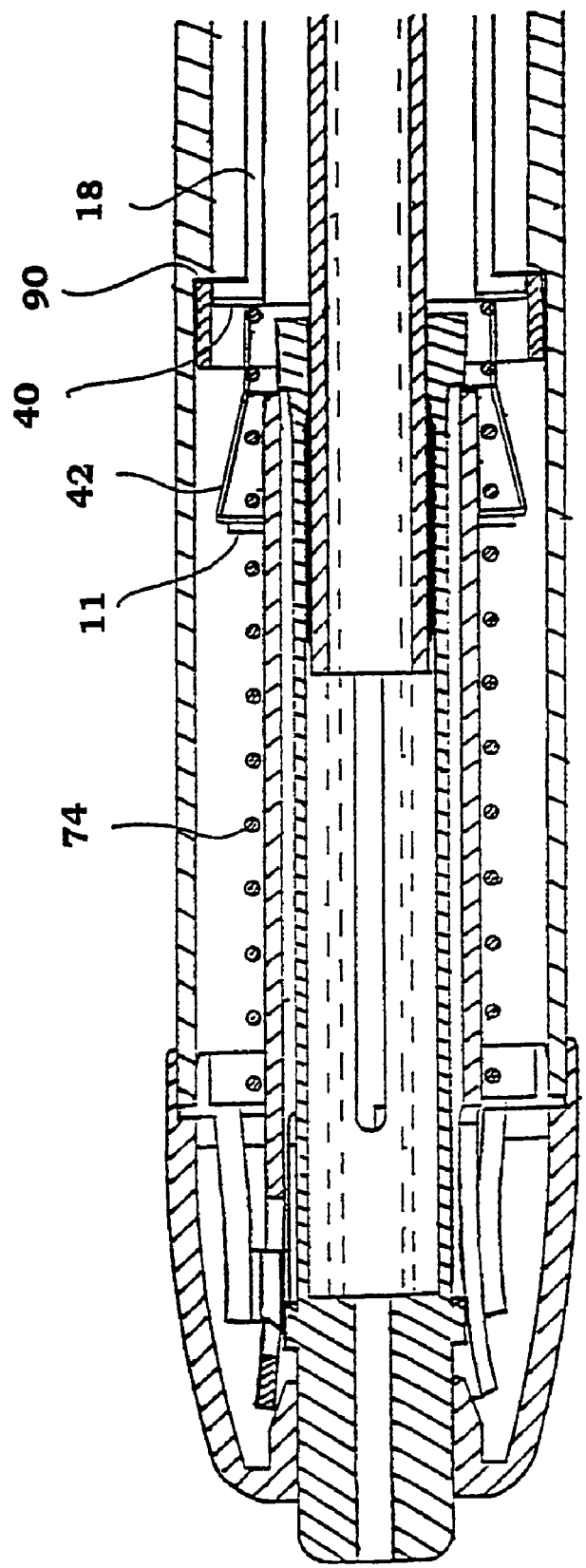
FIG. 9 shows the activation of a needle cover comprised in the auto-injector.

This action enables the activator tube 54 to be pressed into the housing, FIG. 7, and in relation to the rear extension tube, by a finger, whereby the outwardly directed protrusions 60 of the inner end of the activator are moved out of the rear extension tube. Because of the slots of the activator, the inner end will flex outwards and thereby release the plunger from its contact with the activator via the conical surfaces. The release of the plunger 76 will cause it to press against the plunger of the syringe due to the compression spring 82. Due to the incompressibility of the liquid of the syringe and the small diameter of the passage of the needle, the force from the plunger will cause the syringe to move forward whereby the needle 26 will penetrate the end wall 20 of the needle cover and enter into the patient, FIG. 8. The protrusions 28 of the syringe will then abut the inner end 88 of the front end piece, whereby the force from the plunger and the compression spring will cause the plunger of the syringe to move, and thereby the liquid to be injected.

The forward movement of the plunger will cause its ribs 80 to come in contact with the snap fits 32 of the needle cover when the injection movement is almost completed. This causes the front and rear extension tubes to be released from each other, whereby the front extension tube, and thus the needle cover because it is abutting the rear end of the needle cover, are urged forward by the compression spring 74. When the patient removes the injector, the compression spring pushes the needle cover out of the housing, thereby covering the needle, until its ledge 36 abuts a shoulder 90 on the inner wall of the housing, FIG. 9. The arms 42 of the lock ring have then been moved in position corresponding to the openings 11 of the housing and pushed into these by the elasticity of the arms. If one tries to push the needle cover in again, the protrusions 44 of the arms will prevent this by stopping against the surfaces of the openings. The needle cover is further prevented from being pulled out from the front end piece, FIG. 2, because of a ledge 92 on the outer surface of the needle cover and a ledge 94 on the inner surface of the front end piece.

Figure 10:
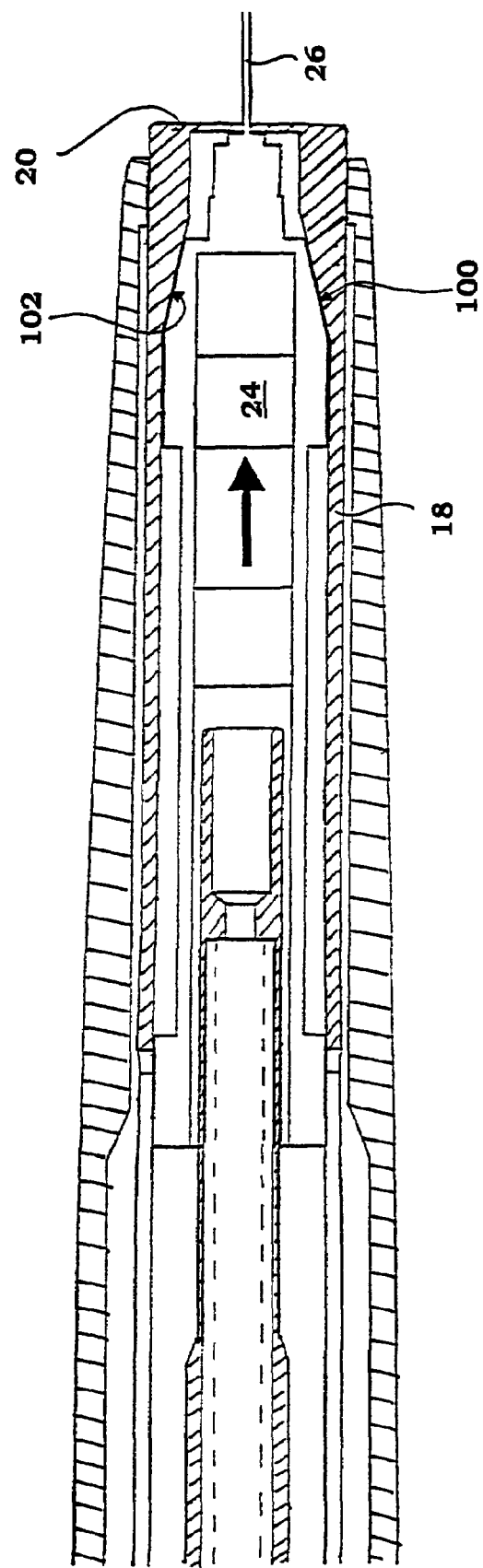
FIG. 10 shows a variant of a holding means for a syringe arranged in the auto-injector.

FIG. 10 shows a variant of holding means for stopping and holding the syringe when injecting the medicament instead of the protrusions 28 as described above. In this case the front end of the syringe is arranged with a somewhat conical surface 100 and the inner surface of the front portion of the needle cover 18 is arranged with a corresponding conical surface. When the syringe is moved forward after activation the conical surfaces meet and will retard the movement of the syringe. The syringe is now held in position when the plunger is pushed into the syringe. The conical surfaces have two advantages that are useful for some applications. Firstly the conical surfaces provide a softer stop of the syringe thereby preventing, or at least greatly reducing, the risk of breakage of the syringe when it is stopped. Secondly, with this arrangement the syringe is held at it's strongest point, which also prevents breakage. This also enables the ability to adjust spring forces to fine tune the device to various friction forces when the syringe is moved. It should be understood that the holding means may have many different configurations in order to obtain the desired function. For example, resilient material may be arranged at the front portion of the needle cover in order to catch and hold the syringe. It is also to be understood that the conical surfaces or the resilient material may be arranged in other parts of the device than the needle cover if the device is configured differently.

In a further variant of the present invention, for facilitating the manufacture of the auto-injector as regards sterilising the needle, it is conceivable to exclude a major portion of the end wall of the needle cover and to have a conventional needle cover of rubber or plastic pushed on the needle, in the way that sterilised syringes normally are delivered after filling and sterilisation, where the needle cover of the syringe preferably protrudes somewhat outside the needle cover of the auto-injector. Before use of the auto-injector, the user removes the needle cover of the syringe, after which the auto-injector is used as described above. With this variant, the needle may be sterilised before assembly in the auto-injector, which, in terms of manufacture, is a simpler step than sterilising the front part of the auto-injector and syringe, that has to be done if the interior of needle cover of the auto-injector is used as a sterile environment.

With the present invention, it is also conceivable that, instead of activating the needle cover in order to extract it from the auto-injector body at the end of the injection cycle for covering the needle afterwards, the syringe is pushed back into the auto-injector body at the end of the injection cycle by appropriate means.

Even though the auto-injector described is utilizing a syringe, it is to be understood that other appropriate drug containers can be used, such as cartridges, ampoules and the like.

It is also conceivable to arrange the auto-injector with some kind of "emergency situation" means. This type of means will disable the need for performing said two-step operation. This may for example be done by having a member, such as a sliding button on the housing, by which the rear extension tube may be pushed backwards whereby the end of the rear extension tube and the arms of the locking device will flex outwards, thereby releasing the activator tube. The member is preferably held in this position after being placed there. The auto-injector can now be activated by merely pushing the activator tube.

This may be useful when a patient has an acute need for medicament, such as an acute allergic attack, and it might be too difficult or time consuming to remember the two-step operation as described above. In this case, a quick slide of the "emergency" button immediately sets the injector ready for injection.

It is to be understood that the embodiments described above and shown on the drawings are to be regarded as non-limiting examples of the present invention, and that it may be modified within the scope of protection as defined by the patent claims.

The invention claimed is:

1. Device for auto-injection of a dose of medicament, comprising:
   a housing arranged to contain a medicament container therein and comprising a needle cover with a contact part intended to be applied against an injection site,
   spring means capable of, upon activation, pushing the needle past the end of the needle cover as well as operating the medicament container to supply the dose of medicament,
   first locking means capable of locking the spring means in a pressurized state,
   first activating means capable of, upon manual operation, releasing the spring means for injection,
   second locking means capable of locking the first activating means,
   second activating means comprising the needle cover, capable of releasing the second locking means when the contact part is exposed to pressure,
   wherein the first locking means is arranged and designed such that the second locking means is also capable of locking the first locking means for preventing the spring means from being released when the device is operated in a sequence in which the first activating means is depressed, held depressed, and then the second activating means is exposed to pressure.

2. Device according to claim 1, wherein the first locking means further is arranged and designed such that the second locking means is prevented from being released if the first activating means is operated at the same time as the second activating means is exposed to pressure.

3. Device according to claim 1, wherein the needle cover surrounds a needle arranged to the medicament container and extends at least the length of the needle.

4. Device according to claim 3, further comprising:
   second spring means capable of pushing the needle cover over the needle after injection,
   third locking means capable of locking the second spring means in a pressurized state during injection, and
   third activating means capable of releasing the second spring means upon end of injection.

5. Device according to claim 4, further comprising a fourth locking means capable of locking the needle cover in a covering position after injection.

6. Device according to claim 1, wherein the needle cover completely encloses a needle and the needle is sterile.

7. Device according to claim 1, further comprising holding means capable of retardation of the movement of the medicament container.

* * * * *